| United States Patent [19] | [11] | 4,331,764 |
|---|---|---|
| Scheit et al. | [45] | May 25, 1982 |

[54] SEMINAL PLASMA RIBONUCLEASE AND METHOD FOR ITS RECOVERY

[75] Inventors: Karl H. Scheit, Göttingen, Fed. Rep. of Germany; Ergam R. S. P. Reddy, Hyderabad, India; Tangirala R. Murti, Hyderabad, India; Madhusudan W. Pandit, Hyderabad, India; Pushpa M. Bhargava, Hyderabad, Anoh, India

[73] Assignee: Max-Planck-Gesellschaft, Göttingen, Fed. Rep. of Germany

[21] Appl. No.: 134,042

[22] Filed: Mar. 26, 1980

[30] Foreign Application Priority Data

Mar. 26, 1979 [DE] Fed. Rep. of Germany ....... 2911867

[51] Int. Cl.$^3$ .............................................. C12N 9/22
[52] U.S. Cl. ....................................... 435/199; 435/6; 435/172
[58] Field of Search ......................................... 435/199

[56] References Cited

PUBLICATIONS

Methods in Enzymology, vol. 6, pp. 828–829, (1963).

*Primary Examiner*—Lionel M. Shapiro
*Attorney, Agent, or Firm*—Felfe & Lynch

[57] ABSTRACT

The new enzyme, seminal plasma ribonuclease, has a content of 1 mole of cysteine per mole, a $K_M$ of 0.42 mM against poly-r-U, a $K_M$ of 0.51 mM against poly-r(A-U) transcript, and is inactive against native RNA. It is obtained either by placing dialyzed seminal plasma on an anion exchanger and then on a cation exchanger and purifying the fraction not adsorbed on the cation exchanger by affinity chromatography, after a gel chromatography step if desired, or by subjecting it directly to affinity chromatography, a support material being used for the affinity chromatography which bears native RNA or a non-hydrolyzable analog of the enzyme substrate.

4 Claims, 2 Drawing Figures

SEMINAL PLASMA RIBONUCLEASE AND METHOD FOR ITS RECOVERY

The invention concerns seminal plasma ribonuclease as a new product, and its preparation and its use.

Seminal plasma ribonuclease, hereinafter referred to as RNAase SPL, occurs as a by-product in the isolation of seminalplasmin, which is described in the simultaneously filed patent application Ser. No. 134,041 filed Mar. 26, 1980.

The RNAase SPL in accordance with the invention has a strong nucleolytic activity and is pyrimidine-specific. Its activity in the case of single-strand synthetic polyribonucleotides, such as poly-r-U or nascent RNA chains which are just being synthesized, often exceeds that of RNAase A. Like the latter it inhibits in vitro transcription, but, unlike RNAase A, it is also highly active against double-strand RNAs, such as poly-r-(A-U).

Studies have shown a nucleolytic activity which is several times greater than in the case of the known RNAase A. With poly-r-U as substrate, the $K_M$ was found to be 0.42 mM (according to Lineweaver-Burk); the $V_{max}$ amounts to 300 micromoles of released UMP-/minute/mg. From this it appears that the affinity of RNAase SPL for poly-r-U is not especially high, but the frequency is great (8400 mol UPM/minute/mol, calculated on the basis of an MG of the enzyme of 28000).

RNAase SPL also hydrolyzes cyclic CMP. The $K_m$ for this substrate amounts to 1 mM, as compared with 3.3 mM for RNAase A. RNAase SPL shows no activity with respect to poly-r-A.

On the basis of the above properties, RNAase SPL can be used as an effective inhibitor of transcription. For example, in a connection of 4.2 μg/ml of RNAase SPL, the preformed transcript of PT$_7$ DNA that develops decomposes very rapidly. Its activity with respect to tagged double-strand RNA (a preformed transcript of poly-d (A-T)) is an order of magnitude greater than it is in the case of RNAase A. At a concentration in which RNAase A has little or no nucleolytic activity against the transcript, poly-r (A-U), RNAase SPL completely hydrolyzes this substrate. The $K_M$ for this substrate was found to be 0.51 mM, and the $V_{max}$ to be 160 μmol of ApU residues per minute per mole.

Although the nucleolytic activity of RNAase SPL on synthetic polyribonucleotides, single-strand or double-strand, clearly exceeds that of RNAase A, RNAase SPL shows only extremely limited activity against natural RNAs, such as for example rat liver RNA or E. coli RNA which have not been depleted of $Mg^{2+}$, i.e., are in the native state. t-RNA is not attacked at all. This is surprising, because hitherto no RNAase of comparable selective action has been known.

On the basis of these properties, the RNAase SPL of the invention is suitable for distinguishing between native and non-native, naturally occurring RNAs.

The amino acid composition of RNAase SPL from cattle semen is shown in the following table.

TABLE

|  | Moles | (moles per mole of protein) |
|---|---|---|
| Lysine | 20 | 8.62 |
| Arginine | 10 | 4.31 |
| Histidine | 9 | 3.88 |
| Aspartic acid + asparagine | 19 | 4.31 |
| Glutamic acid + glutamine | 22 | 9.48 |
| Phenylalanine | 8 | 7.33 |
| Tyrosine | 10 | 4.31 |
| Proline | 22 | 9.48 |
| Methionine | 11 | 4.74 |
| Hemicysteine | 1 | 0.43 |
| Threonine | 18 | 7.76 |
| Serine | 22 | 9.48 |
| Alanine | 17 | 7.33 |
| Glycine | 13 | 5.60 |
| Valine | 18 | 7.76 |
| Leucine | 6 | 2.59 |
| Isoleucine | 6 | 2.59 |
| Total | 232 |  |

The process of the invention for preparing seminal serum RNAase is characterized in that dialyzed seminal plasma either is placed on an anion exchanger and then on a cation exchanger and the fraction that is not adsorbed onto the cation exchanger is purified in some cases, after a gel chromatography step if desired, by affinity chromatography, or it is subjected directly to affinity chromatography using a support material for the affinity chromatography which bears native RNA or a non-hydrolyzable analog of the enzyme substrate.

This process and preferred embodiments thereof will be further described hereinbelow in conjunction with the appended drawing. In this drawing.

STEP I

Mammal semen, cattle semen for example, is separated into its components, seminal plasma and spermatozoa, for example by centrifugation at 500 to 700 g for a period of 5 to 15 minutes at a temperature between 0° and 4° C., and by another centrifugation of the supernatant liquid (seminal plasma) at 1200 to 1600 g for different periods of time of 20 to 60 minutes.

STEP II

The supernatant solution obtained in Step I is dialyzed against a suitable buffer, pH 5 to 9, preferably against tris-HCl buffer, and at a pH between 6.5 to 8.5.

STEP III

The dialyzed seminal plasma of Step II is treated with an anion exchanger, preferably a weakly basic anion exchanger, such as carbohydrate-base exchangers bearing diethylaminoethanol groups (such as DEAE Sephadex of the firm Pharmacia, Sweden).

STEP IV

Figure 2:
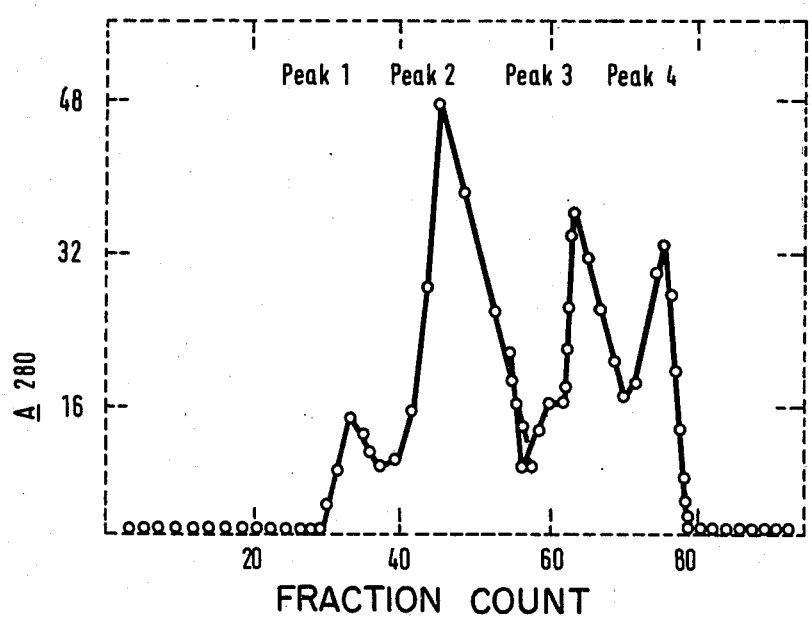
FIG. 2 shows the results of a typical fractional elution in the cation exchanger step.

The unabsorbed protein fraction is placed on a cation exchanger, preferably a weakly acid cation exchanger, such as a carbohydrate-base exchanger bearing carboxymethyl groups (such as CM-Sephadex of the firm Pharmacia, Sweden), and the absorbed protein is eluted with a buffer, such as tris-HCl buffer for example, with the addition of a salt, e.g., with an ion gradient of 0 to 0.8 M, e.g., with sodium chloride. Thus four peaks (i.e., protein fractions) are generally obtained. A typical eultion is shown in FIG. 2, which shows the ultraviolet absorption at 280 nm in the fractions. Occasionally the third and fourth peaks are not separate from one another and together form only one peak.

STEP V

The individual elution fractions, of which the third and fourth (if they are obtained) are protein fractions, are combined and they are dialyzed with the formation of crude RNAase SPL, and lyophilized.

STEP VI

The crude RNAase SPL is further purified by gel filtration (molecular sieve fractionation). Preferably crude RNAase SPL is chromatographed on a column with cross-linked dextran, such as "Sephadex G-75" of the firm Pharmacia, Sweden. Normally three protein fractions are thus obtained (fraction 1, fraction 2 and fraction 3). Occasionally fraction 1 occurs only as a rise on the ascending edge of fraction 3.

STEP VII

Fraction 2 and the ascending portion of fraction 3 in step VI are combined, dialyzed and lyophilized.

STEP VIII

The lyophilized product of Step VII is further purified to homogeneity by purification processes such as polyacrylamide gel electrophoresis, electrophoresis, ion exchanger chromatography, or affinity chromatography, with the formation of pure RNAase SPL.

Figure 1:
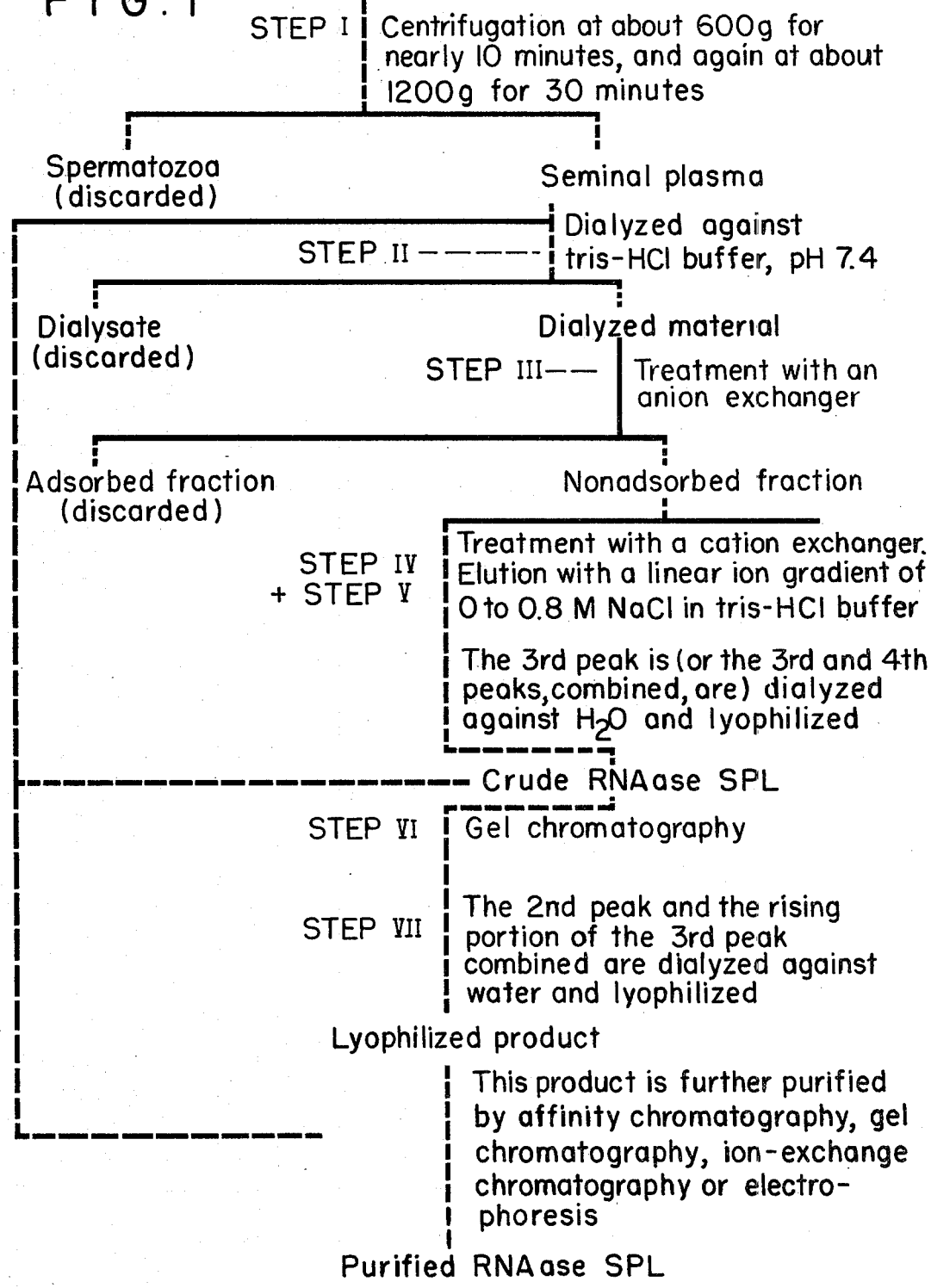
FIG. 1 is a flow diagram of the process.

FIG. 1 represents diagrammatically the course of the method of purification set forth above.

Another preferred embodiment of the refinement process consists in the chromatography of the crude RNAase SPL (Step V) on an affinity column prepared from agarose, to which a non-hydrolyzable analog of the substrate of the enzyme, such as 5'-(p-aminophenylphosphoryl)-2'(3')-uridine phosphate, has been covalently bound. The RNAase SPL is selectively adsorbed on the column and can be eluted by a solution of higher ion concentration, such as 2.0 M NaCl, for example, or a solution of low pH, such as 0.2 M acetic acid. This chromatography is also especially suitable for Step VIII.

Alternatively the purification can also be performed by chromatography of the dialyzed seminal plasma (Step I or Step II) on an affinity chromatography material prepared from cellulose, to which the RNA, such as cattle spermatozoa RNA, has been covalently bound. Only the RNAase SPL, and no other protein of seminal plasma, is absorbed onto this column and is able to be eluted with a solution of high ionic strength, such as 2.0 M NaCl.

The preparation of RNAase SPL can be accomplished, for example, by dialyzing seminal plasma and then chromatographing on a weakly basic anion exchanger having a content of diethylaminoethyl groups, bound to be carbonhdrate-base support (e.g., DEAE-Sephadex of the firm Pharmacia of Sweden. The unabsorbed fraction is placed on a weakly acid cation exchanger such as a carbohydrate-base exchanger bearing carboxymethyl groups (e.g., DM-Sephadex of Pharmacia of Sweden), whereupon three to four peaks are obtained. The third (and fourth, if obtained) peak contains both seminalplasmin and RNAase SPL. The fractions of these two peaks are combined and then chromatographed on a molecular sieve column, preferably a cross-linked dextran, such as Sephadex G-75, for example. Thus two to three peaks are obtained. Most of the RNAase SPL is located in the second (or second and third) peak. Subsequent chromatography of the nucleasecontaining fractions on an affinity chromatography column (preferably [5'-(p-aminophenylphosphoryl)-2'(3')-uridine-phosphate]-agarose) leads to the binding of the RNAase SPL to the column. By elution with 0.2 m acetic acid, pure RNAase can be obtained, which is obtainable in the solid state by lyophilization. The average yield after affinity chromatography amounted to approximately 12 mg per 100 ml of seminal plasma. The yield amounts to about 10%.

RNAase SPL prepared as described above, when subjected to polyacrylamide gel electrophoresis (PAGE) with or without sodium dodecylsulfate (SDS), gave a single band; in isoelectrical focusing on gels or on a column it gave a single band corresponding to an isoelectrical point of pH 9, and in sedimentation tests in an analytical ultracentrifuge it gave a single symmetrical peak (2.6 S).

RNAase SPL of the invention differs considerably from the known cattle ribonuclease (RNAase A), for example with regard to the amino acid composition and the fingerprints. While RNAase A contains 8 moles of cysteine per mole, RNAase SPL has only 1 mole of cysteine per mole.

By various methods, molecular weights between 17,000 and 28,000 have been obtained. By two different SDS-PAGE methods molecular weight values of 17,000 and 17,300 were obtained, and 28,000 in the analytic ultracentrifuge. The amino acid composition corresponds to MG 25726. It is possible that RNAase SPL consists of two non-covalently bound subunits which can not be separated by polyacrylamide gel electrophoresis with SDS (PAGE-SDS).

RNAase SPL does not appear to penetrate into cells, whether procaryotic or eucaryotic. However, it completely inhibits the synthesis of RNA, i.e., the transcription process in vitro. This is because the RNA is decomposed as rapidly as it is produced.

RNAase SPL (crude or pure) can be used for the following purposes:
(a) The hydrolysis of ribonucleic acids, with the exception of native $Mg^{2+}$-rich, naturally occurring ribonucleic acids, at high speed, especially, when only cleavage at the pyrimidine loci in the RNA is desired.
(b) For the hydrolysis of double-strand RNAs, with the exception of native $Mg^{2+}$-rich, naturally occurring RNA, at a high rate.
(c) For determining whether or not a special RNA sample is in the native state.

The following examples explain the preparation of RNAase SPL in accordance with the invention.

EXAMPLE 1

Bull semen collected by means of an artificial vagina is centrifuged at 600 g for several minutes (e.g., 10 to 15 minutes) at 4° C. The supernatant solution (seminal plasma) is finally centrifuged at 1400 g for 30 minutes at 4° C. The supernatant solution is placed in a dialysis bag and dialyzed against tris-HCl buffer with a pH of about 7.4. The dialyzed product is then placed on an anion exchanger ("DEAE-Sephadex" of Pharmacia, Sweden). The unadsorbed fraction from the column of the anion exchanger is placed on a cation exchanger ("CM-Sephadex" of Pharmacia of Sweden). The protein material adsorbed on the cation exchanger is eluted with tris-HCl buffer, pH 7.4, using a gradient of 0 to 0.9 M sodium chloride. The fractions of the third and fourth peaks (or of the third peak if the two peaks are not separate) are combined, dialyzed against water, and lyophilized to form crude RNAase SPL.

The crude RNAase SPL is refined by gel filtration (Sephadex G-75 of Pharmacia, Sweden). The fractions which are active, i.e., show a ribonucleolytic activity, are combined, dialyzed against water, and lyophilized. The lyophilized material is purified on an affinity column charged with agarose-5'-(p-aminophenylphosphoryl)-2'(3')-uridine phosphate.

EXAMPLE 2

The procedure described in Example 1 is followed, but the dialyzed seminal plasma is placed directly on a column with agarose-5'-(p-aminophenylphosphoryl)-2'(3')-uridine phosphate. The product is the same as that of Example 1, but the yield is lower.

Yields:

Crude RNAase SPL, up to 200 mg/100 ml of bull semen,

Pure RNAase SPL, up to 50 mg/100 ml of bull semen.

EXAMPLE 3

The hydrolysis of nucleic acid by the nuclease of the invention was performed in tris-HCl buffer, pH 7.8, using a total volume of 0.1 ml, wherein the corresponding amounts of substrate and enzyme are contained. The reaction mixture is incubated at 37° C. for 5 to 10 minutes, and then the reaction is started by the addition either of the substrate (if different enzyme concentrations were used) or of the enzyme (if different substrate concentrations were used). After given periods of time, aliquots of 10 to 20 microliters of the reaction mixture were chromatographed for 45 minutes using ethanol and ammonium acetate (1 M) (1:1) on Whatmann No. 3 filter paper. Then the paper strips were cut up and tested for non-acid-soluble contents which are taken as an index of the amount of non-hydrolyzed RNA. The measure of the hydrolysis was calculated by the difference.

For the hydrolysis of cyclic CMP, it was performed for 10 minutes in 0.05 M tris-HCl buffer, pH 7.0, containing 0.05 M NaCl and 10 mM $MgCl_2$ in a total volume of 2 ml. The hydrolysis was pursued by measuring the reduction in $E_{290}$ cCMP-$E_{290}$ CMP=$0.74 \times 10^3$.

We claim:

1. Seminalplasma ribonuclease, characterized in that said ribonuclease has a content of 1 mole of cysteine per mole, a $K_M$ of 0.42 mM with respect to poly-r-U, a $K_M$ of 0.51 mM with respect to poly-r-(A-U)-transcript, and is inactive with respect to native RNA.

2. Method for the recovery of seminalplasma ribonuclease of claim 1, characterized in that dialyzed seminal plasma either is placed on an anion exchanger and then on a cation exchanger and the fraction not absorbed on the cation exchanger is purified if desired, after a gel chromatography step, by affinity chromatography, or it is subjected directly to the affinity chromatography, a support material being used for the affinity chromatography which bears native RNA or a non-hydrolyzable analog of the enzyme substrate.

3. Method of claim 2, characterized in that [5'-(p-aminophenylphosphoryl)-2'(3')-uridinephosphate]-agarose is used for the affinity chromatography.

4. Method of claim 2 or 3, characterized in that the affinity chromatography material is eluted with a solution of high ion concentration or/and acid pH value.

* * * * *